(12) United States Patent
Vanoppen et al.

(10) Patent No.: US 7,022,824 B2
(45) Date of Patent: Apr. 4, 2006

(54) METHOD FOR THE PRODUCTION OF SORBIT

(75) Inventors: Dominic Vanoppen, Kapellen (BE); Melanie Maas-Brunner, Mannheim (DE); Ulrich Kammel, Speyer (DE); Jan-Dirk Arndt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/479,967

(22) PCT Filed: Jun. 10, 2002

(86) PCT No.: PCT/EP02/06349

§ 371 (c)(1),
(2), (4) Date: Dec. 11, 2003

(87) PCT Pub. No.: WO02/100539

PCT Pub. Date: Dec. 19, 2002

(65) Prior Publication Data

US 2004/0171889 A1 Sep. 2, 2004

(30) Foreign Application Priority Data

Jun. 11, 2001 (DE) ................. 101 28 203

(51) Int. Cl.
*C07H 1/00* (2006.01)
*C07C 31/18* (2006.01)

(52) U.S. Cl. .................... 536/1.11; 536/124; 568/863; 568/861

(58) Field of Classification Search ............. 536/1.11, 536/124; 568/863, 861
See application file for complete search history.

(56) References Cited

U.S. PATENT DOCUMENTS 2,868,847 A * 1/1959 Gilman ................... 568/863
3,963,788 A 6/1976 Kruse et al.
3,963,789 A 6/1976 Kruse et al.
4,072,628 A 2/1978 Wright et al.
4,380,680 A 4/1983 Arena
4,413,152 A 11/1983 Arena
4,471,144 A 9/1984 Arena
4,487,980 A 12/1984 Arena
4,503,274 A 3/1985 Arena
4,950,812 A 8/1990 Jacobs et al.
5,334,790 A 8/1994 Richard et al.

FOREIGN PATENT DOCUMENTS

EP 0 992 475 4/2000
FR 2 526 782 11/1983

OTHER PUBLICATIONS

Gary L. Haller et al. : "The effect of silica support texture and anion of Impregnating solution on Ru dispersion and on Ru-Cu Interaction" Journal of Catalysis, vol. 84, pp. 477-479 1983.

H. Schiweck et al.: "Sugar alcohols" Ullmann's Encyclopedia of Industrial Chemistry, 5$^{th}$ ed. vol. A 25, pp. 413-437 1994.

* cited by examiner

*Primary Examiner*—Samuel Barts
*Assistant Examiner*—Michael C. Henry
(74) *Attorney, Agent, or Firm*—Oblon, Spivak, McClelland, Maier & Neustadt, P.c.

(57) ABSTRACT

A process is described for preparing sorbitol by catalytic hydrogenation of a monosaccharide forming sorbitol on hydrogenation in the liquid phase, which comprises the catalyst being obtainable by:
  i) single or multiple treatment of an amorphous silicon dioxide based support material with a halogen-free aqueous solution of a low-molecular-weight ruthenium compound and subsequent drying of the treated support material at below 200° C.,
  ii) reducing the solid obtained in i) with hydrogen at from 100 to 350° C.,
step ii) being carried out immediately after step i).

16 Claims, No Drawings

METHOD FOR THE PRODUCTION OF SORBIT

BACKGROUND OF THE INVENTION

1. Field of the Invention

The present invention relates to a process for preparing sorbitol by catalytic hydrogenation of suitable mono- and disaccharides.

2. Description of the Background

Sorbitol is prepared industrially by catalytic hydrogenation of glucose, fructose, sucrose or invert sugar (see H. Schiweck et al. "Sugar Alcohols" in Ullmann's Encyclopedia of Industrial Chemistry, 5th ed. on CD-ROM). For this purpose, the catalysts used to date have primarily been nickel catalysts, for example supported nickel catalysts or Raney nickel. However, there have also been several reports on the use of ruthenium-containing catalysts for this purpose. Generally, the ruthenium catalysts are supported catalysts that contain ruthenium on an oxidic support or an organic support such as carbon.

U.S. Pat. No. 4,380,680, U.S. Pat. No. 4,487,980, U.S. Pat. No. 4,413,152 and U.S. Pat. No. 4,471,144 describe the preparation of sorbitol by catalytic hydrogenation of glucose, in which catalysts are used that contain ruthenium on a support material which is stable under hydrothermal conditions. Hydrothermal support materials which are proposed are alpha-alumina (U.S. Pat. No. 4,380,680), titanium (IV) oxide (U.S. Pat. No. 4,487,980), titanium(IV)-halide-treated alumina (U.S. Pat. No. 4,413,152) and theta-alumina (U.S. Pat. No. 4,471,144).

U.S. Pat. No. 4,503,274 discloses catalysts for hydrogenating glucose to sorbitol which are prepared by impregnating a hydrothermally stable support with an aqueous ruthenium halide solution and subsequently hydrogenating the solid at from 100 to 300° C.

U.S. Pat. No. 3,963,788 describes hydrogenating corn starch hydrolyzates to sorbitol in the presence of ruthenium catalysts in which the ruthenium was supported by an aluminosilicate-based specific zeolite. U.S. Pat. No. 3,963,789 proposes as support for ruthenium catalysts crystalline aluminosilicate clays, in particular montmorillonite.

FR-A 2526782 describes the use of a ruthenium chloride prepared by reacting sodium chloride and ruthenium via $Na_2RuCl_6$ for preparing silica-supported ruthenium catalysts for hydrogenating mono- and oligosaccharides, for example for preparing sorbitol.

The processes known from the prior art for preparing sorbitol by hydrogenation in the presence of ruthenium catalysts, owing to the only moderate activity of the catalysts, give sorbitol only with moderate space-time yields, based on the catalyst used. In view of the high costs of ruthenium, therefore, the economic efficiency of these processes leaves something to be desired. In addition, the selectivities of the catalysts are not sufficient, so that additional expenditure is required in isolating the products of value. In particular, epimerization of the hydroxyl groups is frequently observed.

SUMMARY OF THE INVENTION

It is an object of the present invention, therefore, to provide a process for preparing sorbitol by catalytic hydrogenation of the corresponding mono- or oligosaccharides which form sorbitol on hydrogenation, which process gives sorbitol with improved space-time yields and has a comparable or improved selectivity with regard to the formation of sorbitol, i.e. in which not more or preferably fewer by-products are produced than in the processes of the prior art.

We have found that this object is achieved, surprisingly, by the use of ruthenium catalysts which are obtainable by:

i) single or multiple treatment of an amorphous silicon dioxide based support material with a halogen-free aqueous solution of a low-molecular-weight ruthenium compound and subsequent drying of the treated support material at below 200° C., preferably ≦180° C. and in particular ≦150° C., ii) reducing the solid obtained in i) with hydrogen at from 100 to 350° C., preferably 150 to 350° C. and in particular 200 to 320° C., step ii) being carried out immediately after step i).

DETAILED DESCRIPTION OF THE PREFERRED EMBODIMENTS

Therefore, the present invention relates to a process for preparing sorbitol by catalytic hydrogenation of a monosaccharide which forms sorbitol on hydrogenation in the liquid phase, which comprises the catalyst being selected from the above defined ruthenium catalyst. These catalysts are novel and are subject matter of a parallel German patent application 10128205.2.

Suitable starting materials for preparing sorbitol by the route of catalytic hydrogenation are glucose, fructose and gulose, and glucose-containing products, such as invert sugar, which is obtained by hydrolyzing sucrose. A preferred starting material is D-glucose, and glucose-rich syrups, such as corn starch hydrolyzates, wheat starch hydrolyzates and potato starch hydrolyzates. Preparing D-sorbitol by hydrogenating the D-form of the abovementioned monosaccharides is of particular interest.

It is postulated that the high activity of the catalysts used in the inventive process can be ascribed to the particularly good distribution of the ruthenium on the surface of the support material and to the substantial absence of halogen in the support material. As a result of the manner of preparation, the ruthenium is present in the inventive catalysts as metallic ruthenium. Electron microscopy studies (TEM) of the catalysts have found that the ruthenium is present on the support material as an atomic dispersion and/or in the form of ruthenium particles which are present virtually exclusively, that is to say more than 90%, preferably more than 95%, based on the number of visible particles, as isolated particles having diameters less than 10 nm, in particular less than 7 nm. In other words, the catalyst essentially contains no ruthenium particles having diameters greater than 10 nm, that is to say less than 10%, in particular less than 5% ruthenium particles and/or agglomerates of ruthenium particles having diameters greater than 10 nm. Owing to the use of halogen-free ruthenium precursors and solvents in the preparation, the chlorine content of the inventively used catalysts is in addition less than 0.05% by weight (<500 ppm), based on the total weight of the catalyst. Here and in the text below, all ppm data are to be understood as meaning parts by weight, unless stated otherwise.

An essential constituent of the catalysts used in the inventive process is the amorphous silicon dioxide based support material. The term "amorphous" in this context means that the content of crystalline silicon dioxide phases makes up less than 10% of the support material. The support materials used for preparing the catalysts can, however, have superstructures which are formed by regular disposition of pores in the support material.

Support materials which come into consideration are in principle all amorphous silicon dioxide types that consist of at least 90% by weight silicon dioxide, the remaining 10% by weight, preferably no more than 5% by weight, of the support material also being able to be another oxidic material, for example MgO, CaO, $TiO_2$, $ZrO_2$, $Fe_2O_3$ or alkali metal oxide. Obviously, the support material used is also halogen-free, that is to say the halogen content is less than 500 ppm, based on the total weight of the support material. Preferably the support material contains no more than 1% by weight, and in particular no more than 0.5% by weight, and in particular no detectable amounts (<500 ppm), of aluminum oxide, calculated as $Al_2O_3$. In a preferred embodiment support materials are used which contain less than 500 ppm of $Fe_2O_3$. The proportion of alkali metal oxide generally results from the preparation of the support material, and can be up to 2% by weight. Frequently, it is less than 1% by weight. Suitable supports are also alkali metal oxide free supports (<0.1% by weight). The proportion of MgO, CaO, $TiO_2$ or of $ZrO_2$ can make up to 10% by weight of the support material and is preferably no more than 5% by weight. However, support materials having no detectable amounts of these metal oxides (<0.1% by weight) are also suitable.

Preference is given to support materials which have a specific surface area from 50 to 700 $m^2/g$, in particular from 80 to 600 $m^2/g$, and especially in the range from 100 to 600 $m^2/g$ (BET surface area as defined in DIN 66131). Among the pulverulent support materials, in particular preference is given to those whose specific (BET) surface area is in the range from 200 to 600 $m^2/g$. In the case of support material in the form of shaped bodies, the specific surface area is in particular from 100 to 300 $m^2/g$.

Suitable amorphous silicon-dioxide-based support materials are familiar to those skilled in the art and are commercially available (see, for example, O. W. Flörke, "Silica" in Ullmann's Encyclopedia of Industrial Chemistry 5th ed. on CD-ROM). They can either be of natural origin or synthetically prepared. Examples of suitable amorphous silicon-dioxide-based support materials are kieselgur, silica gels, pyrogenic silicic acid and precipitated silicic acid. In a preferred embodiment of the invention, the catalysts have silica gels as support materials.

Depending on the embodiment of the inventive process, the support material can have differing forms. If the process is configured as a suspension process, to prepare the inventive catalysts, usually, the support material is used in the form of a finely divided powder. The particle size of the powder particles is preferably from 1 to 200 μm, and in particular from 10 to 100 μm. When the catalyst is used in fixed-bed catalysts, usually shaped bodies of the support material are used, which are obtainable, for example, by extrusion or tableting and which can have, for example, the shape of spheres, tablets, cylinders, strands, rings or hollow cylinders, stars and the like. The dimensions of these shaped bodies usually range from 1 mm to 25 mm. Frequently, catalyst strands are used having strand diameters of from 2 to 5 mm and strand lengths of from 2 to 25 mm.

The ruthenium content in the catalysts can be varied over a wide range. Generally, it is at least 0.1% by weight, preferably at least 0.2% by weight, and frequently does not exceed a value of 10% by weight, in each case based on the weight of the support material and calculated as elemental ruthenium. Preferably, the ruthenium content is from 0.2 to 7% by weight, and in particular from 0.4 to 5% by weight.

The ruthenium catalysts used in the inventive process are generally prepared by firstly treating the support material with a halogen-free aqueous solution of a low-molecular-weight ruthenium compound, termed (ruthenium) precursor hereinafter, in such a manner that the desired amount of ruthenium is taken up by the support material. This step is also termed impregnating hereinafter. The support thus treated is then dried, complying with the above specified upper temperature limits. If appropriate, the resultant solid is then again treated with the aqueous solution of the ruthenium precursor and again dried. This procedure is repeated until the amount of ruthenium compound taken up by the support material corresponds to the desired ruthenium content in the catalyst.

The support material can be treated or impregnated in various ways depending in a known manner on the shape of the support material. For example, the support material can be sprayed or rinsed with the precursor solution, or the support material can be suspended in the precursor solution. For example, the support material can be suspended in the aqueous solution of the ruthenium precursor and after a certain time can be filtered off from the aqueous supernatant. The ruthenium content of the catalyst can then be controlled in a simple manner via the amount of liquid taken up and the ruthenium concentration of the solution. The support material can also be impregnated, for example, by treating the support with a defined amount of the aqueous solution of ruthenium precursor corresponding to the maximum amount of liquid which the support material can take up. For this purpose, the support material can be sprayed, for example, with the required amount of liquid. Suitable apparatuses for this are the apparatuses customarily used for mixing liquids with solids (see Vauck/Müller, Grundoperationen chemischer Verfahrenstechnik [Unit operations of chemical engineering], $10^{th}$ edition, Deutscher Verlag fur Grundstoffindustrie, 1994, pp. 405 et seq.), for example tumbler dryers, impregnating drums, drum mixers, blade mixers and the like. Monolithic supports are usually rinsed with the aqueous solutions of the ruthenium precursor.

The aqueous solutions used for impregnating are according to the invention halogen-free, that is to say they contain no halogen or less than 500 ppm, preferably less than 100 ppm, halogen, based on the total weight of the solution. The ruthenium precursors used are therefore only those ruthenium compounds which do not contain chemically bound halogen and which are sufficiently soluble in the aqueous solvent. These include, for example, ruthenium(III) nitrosylnitrate ($Ru(NO)(NO_3)_3$), ruthenium(III) acetate and the alkali metal ruthenates(IV) such as sodium ruthenate(IV) and potassium ruthenate(IV).

"Aqueous" here is water and mixtures of water containing up to 50% by volume, preferably no more than 30% by volume, and in particular no more than 10% by volume, of one or more water-miscible organic solvents, for example mixtures of water with $C_1$–$C_4$-alkanols such as methanol, ethanol, n-propanol or isopropanol. Frequently, water is used as sole solvent. The aqueous solvent will frequently additionally contain at least one halogen-free acid, for example nitric acid, sulfuric acid, phosphoric acid, or acetic acid, preferably a halogen-free mineral acid, in the solution for stabilizing the ruthenium precursor. In many cases, therefore, a halogen-free mineral acid diluted with water, for example nitric acid diluted to half-concentrated, is used as solvent for the ruthenium precursor. The concentration of ruthenium precursor in the aqueous solutions of course depends on the amount of ruthenium precursor to be added and the absorption capacity of the support material for the aqueous solution and is generally from 0.1 to 20% by weight.

Drying can be performed by the customary processes of solids drying, complying with the abovementioned upper temperature limits. Complying with the inventive upper limit of drying temperatures is important for the quality, that is to say the activity, of the catalyst. Exceeding the above specified drying temperatures leads to a significant loss of activity. Calcining the support at relatively high temperatures, for example above 300° C., or even 400° C., as proposed in the prior art, is not only superfluous, but also has a disadvantageous effect on the catalyst activity. To achieve sufficient drying rates, drying is generally performed at elevated temperature, for example at at least 40° C., in particular at least 70° C. and especially at least 100° C.

The ruthenium-precursor-impregnated solid is usually dried at atmospheric pressure, reduced pressure also being able to be used to promote drying. Frequently, to promote drying, a gas stream, for example air or nitrogen, is passed over or through the material to be dried.

The drying time of course depends on the desired degree of drying and the drying temperature and is generally from 2 h to 30 h, preferably from 4 h to 15 h.

Preferably, the treated support material is dried until the content of water or of volatile solvent constituents, before reduction ii), makes up less than 5% by weight, in particular no more than 2% by weight, and particularly preferably no more than 1% by weight, based on the total weight of the solid. Here, the specified percentages by weight relate to the loss of weight of the solid determined at 300° C., a pressure of 1 bar and for a time of 10 min. In this manner, the activity of the inventive catalysts can be further increased.

Preferably, the drying is performed with agitation of the precursor-solution-treated solid, for example by drying the solid in a rotary kiln or a rotating ball furnace. In this manner the activity of the inventive catalysts can be further increased.

The solid obtained after drying is converted into its catalytically active form according to the invention by hydrogenating the solid at the above specified temperatures in a manner known per se (step ii)).

For this purpose, the support material, at the above specified temperatures, is brought into contact with hydrogen or a mixture of hydrogen and an inert gas. The hydrogen partial pressure is of minor importance for the result of the reduction and will generally be varied from 0.2 bar to 1.5 bar. Frequently the catalyst material is hydrogenated at atmospheric pressure of hydrogen in a hydrogen stream. Preferably, the hydrogenation takes place with agitation of the solid obtained in i), for example by hydrogenating the solid in a rotary kiln or a rotating ball furnace. In this manner the activity of the inventive catalysts can be further increased.

After the hydrogenation, the catalyst, to improve the handleability, can be passivated in a known manner, for example by briefly treating the catalyst with an oxygen-containing gas, for example air, but preferably with an inert gas mixture containing from 1 to 10% by volume of oxygen.

In the inventive process, the monosaccharide is preferably hydrogenated by hydrogenating a solution, preferably an aqueous solution, of the respective monosaccharide, or in the case of invert sugar as starting material, of the monosaccharide mixture. "Aqueous" here is defined as above. Expediently, water is used as sole solvent, which may contain small amounts of a preferably halogen-free acid for setting the pH. In particular, the monosaccharide is used as aqueous solution having a pH from 4 to 10, especially from 5 to 7.

The monosaccharide concentration in the liquid phase can in principle be chosen freely, and is frequently in the range from 10 to 80% by weight, and preferably in the range from 15 to 50% by weight, based on the total weight of the solution.

The actual hydrogenation is usually performed in a similar manner to the known hydrogenation processes for preparing sugar alcohols, as described in the prior art mentioned at the outset. For this purpose the liquid phase containing the monosaccharide is brought into contact with the catalyst in the presence of hydrogen. The catalyst here either can be suspended in the liquid phase (suspension procedure) or the liquid phase is passed through a fluid catalyst bed (fluid-bed procedure) or a fixed catalyst bed (fixed-bed procedure). The hydrogenation can be either continuous or batchwise. Preferably, the inventive process is carried out in trickling reactors by the fixed-bed procedure. The hydrogen can be passed over the catalyst either cocurrently with the solution of the starting material to be hydrogenated, or countercurrently.

Suitable apparatuses for carrying out the hydrogenation by the suspension procedure and also for hydrogenation on a fluid catalyst bed and on a fixed catalyst bed are known from the prior art, for example from Ullmanns Enzyklöpadie der Technischen Chemie [Ullmann's Encyclopedia of Industrial Chemistry], 4$^{th}$ Edition, Volume 13, pp. 135 et seq., and from P. N. Rylander, "Hydrogenation and Dehydrogenation" in Ullmann's Encyclopedia of Industrial Chemistry, 5th ed. on CD-ROM.

Generally, the hydrogenation is carried out at elevated hydrogen pressure, for example at a hydrogen partial pressure of at least 10 bar, preferably at least 20 bar, and in particular at least 40 bar. Generally, the hydrogen partial pressure does not exceed 500 bar, in particular 350 bar. Particularly preferably, the hydrogen partial pressure is in the range from 40 to 200 bar. The reaction temperatures are generally at least 40° C., and frequently do not exceed 250° C. In particular, the hydrogenation process is carried out at from 80 to 150° C.

Owing to the high catalyst activity, comparatively small amounts of catalyst are required based on the starting material used. Thus, in the batchwise suspension procedure, generally less than 1 mol %, for example from $10^{-1\ 3}$ mol % to 0.5 mol % of ruthenium, based on 1 mol sugar is used. In the continuous form of the hydrogenation process, usually the starting material to be hydrogenated is passed over the catalyst at a rate of from 0.05 to 2 kg/(1(catalyst)·h), in particular at a rate of from 0.07 to 0.7 kg/(1(catalyst)·h).

In the inventive process, a solution of sorbitol in the aqueous solvent respectively used is produced, from which the sorbitol can be obtained by known processes (see H. Schiweck et al. "Sugar Alcohols" in Ullmann's Encyclopedia of Industrial Chemistry, 5th ed. on CD-ROM). In the case of the aqueous reaction mixtures preferably obtained, the sorbitol can be isolated, for example, by evaporation with subsequent crystallization (DE-A 2350690, EP-A 32288, EP-A 330352) or spray-drying (DK 133603, DD 277176). If necessary, the catalyst is removed in advance by customary processes and the reaction solution is subjected to decolorization using suitable filter aids and/or treatment with ion exchangers to remove metal ions, gluconates or other organic acids.

When invert sugar or fructose is used, in addition to sorbitol, obviously also mannitol is formed. From the resultant reaction mixtures, sorbitol can be isolated by selective crystallization.

The inventive process is distinguished by the high space-time yields achieved and, when glucose is used as starting material, also by high product selectivity. In addition, the ruthenium catalysts inventively used are distinguished by particularly high service lives, as a result of which the process becomes particularly economically attractive.

Obviously, the catalysts used in this process, when the activity decreases, can be regenerated according to methods known to those skilled in the art which are customary for noble metal catalysts such as ruthenium catalysts. Those which may be mentioned here are, for example, treating the catalyst with oxygen, as described in BE 882279, treatment with dilute halogen-free mineral acids, as described in U.S. Pat. No. 4,072,628, or treatment with hydrogen peroxide, for example in the form of aqueous solutions having a content of from 0.1 to 35% by weight, or treatment with other oxidizing substances, preferably in the form of halogen-free solutions. Usually, the catalyst will be rinsed with a solvent, for example water, after the reactivation and before renewed use.

The examples below serve for more detailed explanation of the invention:

I. Preparation of the Catalysts

1. Protocol A: Pulverulent, Halogen-free Catalyst, Non-calcined.

A defined amount of the respective support material was impregnated with the maximum amount of a solution of ruthenium(III) nitrosylnitrate in water, which could be absorbed by the respective support material. The maximum amount absorbed by the respective support material had been determined in advance on the basis of an authentic sample. The concentration of the solution was such in each case as to result in the desired concentration of ruthenium in the support material.

The resultant solid was then dried for 13 h at 120° C. in a rotary ball oven. The residual water content was less than 1% by weight, determined as the weight loss of a sample dried for 10 minutes at 300° C. and 1 bar.

The resultant solid was reduced at atmospheric pressure in a hydrogen stream at 300° C. in a rotary ball furnace for 4 h. After cooling and rendering inert with nitrogen, the catalyst was passivated by passing over 5% by volume of oxygen in nitrogen for a period of 120 min.

2. Protocol B: Pulverulent, Halogen-free Catalyst, Calcined.

The catalyst was prepared in a similar manner to protocol A, but the solid obtained after drying was heated at 400° C. in an air stream for 4 h before the hydrogenation.

3. Protocol C: Pulverulent, Halogen-containing Catalyst, Non-calcined.

The catalyst was prepared in a similar manner to protocol A, but instead of ruthenium(III) nitrosylnitrate, ruthenium (III) chloride was used.

4. Protocol D: Rod-shaped, Halogen-free Catalyst, Non-calcined.

A defined amount of cylindrical support-material strands (diameter 4 mm, length from 3 to 10 mm) was impregnated with the maximum amount of a solution of ruthenium(III) nitrosylnitrate which could be absorbed by the respective support material. The maximum amount absorbed by the respective support material had been determined in advance on the basis of an authentic sample. The concentration of the solution was such in each case as to result in the desired concentration of ruthenium in the support material.

The resultant impregnated rods were then dried for 13 h at 120° C. in a rotary ball furnace. The residual water content was less than 1% by weight.

The resultant dried rods were reduced in a rotary ball furnace for 4 h at 300° C. in a hydrogen stream at atmospheric pressure. After cooling and rendering inert with nitrogen, the resultant catalyst was passivated by passing over 5% by volume of oxygen in nitrogen for a period of 120 min.

5. Protocol E: Rod-shaped, Halogen-containing Catalyst, Non-calcined.

The catalyst was prepared in a similar manner to protocol D, but ruthenium(III) chloride was used instead of ruthenium(III) nitrosylnitrate.

TABLE 1

| | Catalysts | | |
|---|---|---|---|
| Catalyst No. | Ruthenium content [% by weight] | Protocol | Support |
| K1 | 1 | A | $SiO_2$ Powder[1] |
| K2 (C) | 1 | C | $SiO_2$ Powder[1] |
| K3 (C) | 1 | B | $SiO_2$ Powder[1] |
| K4 | 1 | A | $SiO_2$ Powder[2] |
| K5 | 1 | A | $SiO_2$ Powder[3] |
| K6 | 1 | A | $SiO_2$ Powder[4] |
| K7 (C) | 1 | A | $TiO_2$ Powder[5] |
| K8 (C) | 1 | A | $ZrO_2$ Powder[6] |
| K9 (C) | 1 | A | $\gamma$-$Al_2O_3$ Powder[7] |
| K10 (C) | 1 | A | Activated carbon[8] |
| K11 (C) | 1 | A | H-ZSM 5[9] |
| K12 (C) | 1 | A | Magnesium oxide[10] |
| K13 (C) | 1 | A | Aluminosilicate[11] |
| K14 (C) | 1 | A | $\theta$-$Al_2O_3$ Powder[12] |
| K15 | 1 | D | $SiO_2$ Rods[13] |
| K16 (C) | 1 | E | $SiO_2$ Rods[13] |

C Comparison catalyst
[1] silica gel powder having an $SiO_2$ content > 99.95% by weight, a specific BET surface area of 523 $m^2$/g, a water absorption of 1.4 ml/g, a pore volume of 0.75 ml/g (determined by nitrogen porometry as specified in DIN 66134), a defined pore size of 60 Å a particle size of from 63 to 200 µm;
[2] silica gel powder having an $SiO_2$ content of > 99.95% by weight, a specific BET surface area of 317 $m^2$/g, a water absorption of 1.4 ml/g, a particle size < 63 µm;
[3] silica gel powder having an $SiO_2$ content > 99.95% by weight, a specific BET surface area of 270 $m^2$/g, a water absorption of 1.5 ml/g, a particle size < 63 µm;
[4] silica gel powder having an $SiO_2$ content > 99.5% by weight, a specific BET surface area of 68 $m^2$/g, a water absorption of 1.04 ml/g, a particle size < 63 µm;
[5] titanium dioxide powder having a $TiO_2$ content > 99.9% by weight, a specific BET surface area of 325 $m^2$/g, a water absorption of 0.84 ml/g, a particle size < 63 µm;
[6] zirconium dioxide powder having a $ZrO_2$ content > 99.5% by weight, a specific BET surface area of 138 $m^2$/g, a water absorption of 0.7 ml/g, a particle size of < 63 µm;
[7] gamma-alumina powder having an $Al_2O_3$ content > 99.5% by weight, a specific BET surface area of 226 $m^2$/g, a water absorption of 1.1 ml/g, a pore volume of 0.54 ml/g, a particle size < 63 µm;
[8] activated carbon Norit CAl having a specific BET surface area of 1306 $m^2$/g, a water absorption of 1.7 ml/g;
[9] H-ZSM 5 Zeolite, type ZSM 5 from Vetikon;
[10] magnesium oxide having an MgO content > 99% by weight, a specific BET surface area of 81 $m^2$/g, a water absorption of 3.2 ml/g, a particle size < 63 µm;
[11] aluminosilicate, having an $Al_2O_3$/$SiO_2$ ratio of 30/70 a specific BET surface area of 482 $m^2$/g, a pore volume of 0.33 ml/g, a water absorption of 0.57 ml/g, a particle size of < 63 µm;
[12] theta-alumina powder having an $Al_2O_3$ content > 99.95% by weight, a specific BET surface area of 80 $m^2$/g, a water absorption of 1.05 ml/g, a pore volume of 0.67 ml/g (DIN 66134), a particle size < 100 µm;
[13] silica gel rods (d 4 mm, 1 from 1 to 10 mm) of silica gel having an $SiO_2$ content > 99.5% by weight (0.3% by weight $Na_2O$), a specific BET surface area of 169 $m^2$/g, a water absorption of 0.95 ml/g, a pore volume of 0.7 ml/g (DIN 66134).

II. Hydrogenation of D-glucose in the Suspension Procedure

EXAMPLE 1, COMPARATIVE EXAMPLES C1 TO C3

General Hydrogenation Protocol.

1200 ml of a 30% by weight solution of D(+) glucose in water together with 3 g of the respective catalyst were placed in a 2.5 l autoclave equipped with agitator, apparatuses for sampling and hydrogen pressurization. The catalyst was rendered inert with nitrogen. Then a pressure of 50 bar of hydrogen was established and the autoclave was heated to 120° C. During the reaction, agitation was performed at 1000 rpm. To determine the conversion rate, during the reaction samples were taken every 20 min, and the contents of sorbitol and mannitol were determined by HPLC. The reaction was terminated at the latest after 20 h. Table 2 shows the period required to achieve a maximum yield. In addition, the selectivity with respect to sorbitol formation, and the formation of mannitol as by-product are reported.

TABLE 2

| Example | Catalyst No. | Support | t-max. [h] | Conversion rate [%] | Selectivity [%] | Mannitol [%] |
|---|---|---|---|---|---|---|
| 1 | K1 | SiO$_2$ | 1.5 | 99.7 | 97.9 | 1.08 |
| C1 | K2(C) | SiO$_2$ | 3 | 99.8 | 95.6 | 1.34 |
| C2 | K3(C) | SiO$_2$ | 10 | 99.4 | 99.1 | n.d. |
| C3 | K14(C) | θ-Al$_2$O$_3$ | 20 | 98 | 98.7 | 0.51 |

III Hydrogenation of D-glucose in the Suspension Procedure

EXAMPLES 2 TO 5, COMPARATIVE EXAMPLES C4 to C10

In a similar manner to the general hydrogenation protocol described under II, 180 ml of a 30% by weight solution of D-glucose in water together with 0.9 g of the respective catalyst were hydrogenated in a 300 ml autoclave at 100 bar hydrogen and at 90° C. Conversion rate and selectivity were determined by HPLC as described under II. Table 3 shows the period required to achieve maximum yield. In addition, the selectivity with respect to sorbitol formation is reported.

TABLE 3

| Example | Catalyst No. | Support | t-max. [h] | Conversion rate [%] | Selectivity [%] |
|---|---|---|---|---|---|
| C4 | K7(C) | TiO$_2$ | 22 | 100 | 95.5 |
| C5 | K8(C) | ZrO$_2$ | 44 | 68 | 92.9 |
| C6 | K9(C) | γ-Al$_2$O$_3$ | 17 | 99.6 | 97.8 |
| C7 | K10(C) | Activated carbon | 20 | 100 | >99.5 |
| C8 | K11(C) | H-ZSM 5 | 19 | 100 | 97.0 |
| C9 | K12(C) | MgO | 18 | 92 | 40 |
| C10 | K13(C) | Aluminosilicate | 19 | 100 | 95.7 |
| 2 | K4 | SiO$_2$ | 2 | 100 | >99.5 |
| 3 | K5 | SiO$_2$ | 4 | 100 | >99.5 |
| 4 | K1 | SiO$_2$ | 6 | 100 | >99.5 |
| 5 | K6 | SiO$_2$ | 5 | 100 | >99.5 |

III Hydrogenation of D-glucose in the Presence of a Fixed Catalyst Bed

EXAMPLE 6 AND COMPARATIVE EXAMPLE C11

The reactor used was a heatable stainless steel reaction tube packed with catalyst. The reaction arrangement had a feed pump for the starting materials, a circulation pump, apparatuses for sampling and a separator with level control and exhaust gas control.

240 ml of a 30% strength by weight solution of the respective mono- or disaccharide was circulated in this reaction arrangement at 100° C. and a hydrogen pressure of 50 bar at a rate of 50 ml/(g(catalyst)·h) and during this, by means of the analysis described under II, the decrease in starting material, the increase in products and the formation of by-products were determined. When a conversion rate of 99.4% was achieved, the reaction was terminated. The contact time required to achieve the maximum yield is given in Table 4 together with the selectivity. Contact time=vol.(solution)/vol.(reaction tube)·reaction time

TABLE 4

| Example | Catalyst No. | Support | t-contact [h] | Conversion rate [%] | Selectivity [%] | Mannitol [%] |
|---|---|---|---|---|---|---|
| 6 | K15 | SiO$_2$ | 1.2 | 99.5 | 97.4 | 0.7 |
| C11 | K16(C) | SiO$_2$ | 1.2 | 99.5 | 96.8 | 2.1 |

We claim:

1. A process for preparing sorbitol, comprising:
catalytically hydrogenating a monosaccharide in an aqueous solution in the presence of a ruthenium catalyst to form sorbitol, said ruthenium catalyst being prepared by:
   i) treating an amorphous silicon dioxide based support material with a halogen-free aqueous solution of a low-molecular-weight ruthenium compound in a single treatment or by multiple treatments and then subsequently drying the treated support material at a temperature below 200° C., and then immediately thereafter
   ii) reducing the solid obtained in i) with hydrogen at a temperature ranging from 100 to 350° C.

2. The process as claimed in claim 1, wherein the amorphous silicon dioxide based support has a BET surface area in the range from 50 to 700 m$^2$/g.

3. The process as claimed in claim 2, wherein the amorphous silicon dioxide based support has a BET surface area in the range from 80 to 600 m$^2$/g.

4. The process as claimed in claim 1, wherein the content of crystalline silicon dioxide in the amorphous silicon dioxide support is less than 10%.

5. The process as claimed in claim 1, wherein the ruthenium catalyst contains ruthenium in an amount from 0.2 to 10% by weight, based on the weight of the support.

6. The process as claimed in claim 1, wherein the ruthenium catalyst contains less than 0.05% by weight of halogen, based on the total weight of the catalyst, and consists of:
an amorphous silicon dioxide based support material and elemental ruthenium which is present on the support in an atomic dispersion and/or in the form of ruthenium particles, and
the catalyst is comprised essentially of no ruthenium particles and/or agglomerates thereof that have diameters greater than 10 nm.

7. The process as claimed in claim 1, wherein the treated support material is dried to a water content of less than 5% by weight.

8. The process as claimed in claim 7, wherein said water content is less than 2% by weight.

9. The process as claimed in claim 1, wherein the ruthenium catalyst is passivated by treatment of the catalyst with an oxygen-containing gas.

10. The process as claimed in claim 9, wherein the oxygen-containing gas is air or a mixture of an inert gas with from 1 to 10% by volume of oxygen.

11. The process as claimed in claim 1, wherein the monosaccharide is present in the reaction medium as an aqueous solution having a pH in the range from 4 to 10.

12. The process as claimed in claim 1, wherein the monosaccharide is glucose.

13. The process as claimed in claim 1, wherein the hydrogenation is carried out at a hydrogen partial pressure in the range from 10 to 500 bar.

14. The process as claimed in claim 1, wherein the hydrogenation is conducted at a temperature ranging from 40 to 2500° C.

15. The process as claimed in claim 1, wherein the hydrogenation reaction is conducted on a fixed-bed catalyst.

16. The process as claimed in claim 1, wherein the hydrogenation is conducted in a liquid phase containing the catalyst in the form of a suspension.

* * * * *